United States Patent
Brown et al.

(10) Patent No.: US 9,997,696 B2
(45) Date of Patent: Jun. 12, 2018

(54) METHODS OF MANUFACTURING HIGH FREQUENCY PIEZOCOMPOSITE ULTRASOUND TRANSDUCERS

(71) Applicant: FUJIFILM SonoSite, Inc., Bothell, WA (US)

(72) Inventors: Jeremy Brown, Halifax (CA); F. Stuart Foster, Toronto (CA); Jianhua Yin, Scarborough (CA)

(73) Assignee: FUJIFILM SonoSite, Inc., Bothell, WA (US)

( * ) Notice: Subject to any disclaimer, the term of this patent is extended or adjusted under 35 U.S.C. 154(b) by 259 days.

(21) Appl. No.: 14/203,435

(22) Filed: Mar. 10, 2014

(65) Prior Publication Data

US 2014/0354113 A1    Dec. 4, 2014

Related U.S. Application Data

(63) Continuation of application No. 13/676,031, filed on Nov. 13, 2012, now Pat. No. 8,823,246, which is a
(Continued)

(51) Int. Cl.
*H01L 41/187*    (2006.01)
*H01L 41/27*    (2013.01)
(Continued)

(52) U.S. Cl.
CPC ............ *H01L 41/1876* (2013.01); *A61B 1/06* (2013.01); *B06B 1/0622* (2013.01); *H01L 41/08* (2013.01);
(Continued)

(58) Field of Classification Search
CPC ..... H01L 41/08; H01L 41/1876; H01L 41/25; H01L 41/27; H01L 41/29; H01L 41/33;
(Continued)

(56) References Cited

U.S. PATENT DOCUMENTS 4,354,502 A * 10/1982 Colley .................. A61B 8/12
600/469
4,398,325 A    8/1983 Piaget et al.
(Continued)

FOREIGN PATENT DOCUMENTS

| JP | 62-261300 | | 11/1987 |
| JP | 02121897 A | * | 5/1990 |
| WO | 2009066184 | | 5/2009 |

OTHER PUBLICATIONS

Brown, J.A. et al, "Fabrication and Performance of High-Frequency Geometrically Focused Composite Transducer with Triangular Pillar Geometry", IEEE 2007 Ultrasonics Symposium Oct. 28-31, 2007, pp. 80-83.
(Continued)

*Primary Examiner* — A. Dexter Tugbang
(74) *Attorney, Agent, or Firm* — Perkins Coie LLP

(57) ABSTRACT

Methods of manufacturing transducers with triangular cross-sectional shaped pillars are disclosed herein. According to one aspect of the present application, a plurality of first, second and third troughs are formed in a transducer substrate in first, second and third directions, respectively, to form an array of pillars. In one embodiment, the first direction is substantially parallel to a longitudinal axis of the substrate, the second direction is substantially perpendicular to the longitudinal axis of the substrate, and the third direction is oblique to the longitudinal axis of the substrate. The resulting array of pillars can be configured to suppress lateral modes of a high frequency ultrasound transducer.

18 Claims, 8 Drawing Sheets

Related U.S. Application Data continuation of application No. 12/963,096, filed on Dec. 8, 2010, now Pat. No. 8,310,133, which is a continuation-in-part of application No. 12/192,816, filed on Aug. 15, 2008, now abandoned.

(60) Provisional application No. 60/983,263, filed on Oct. 29, 2007.

(51) Int. Cl.

| | | |
|---|---|---|
| *H01L 41/33* | (2013.01) | |
| *H01L 41/29* | (2013.01) | |
| *H01L 41/25* | (2013.01) | |
| *H01L 41/08* | (2006.01) | |
| *A61B 1/06* | (2006.01) | |
| *B06B 1/02* | (2006.01) | |
| *B06B 1/06* | (2006.01) | |
| *A61B 8/12* | (2006.01) | |
| *G01S 15/89* | (2006.01) | |

(52) U.S. Cl.
CPC .............. *H01L 41/25* (2013.01); *H01L 41/27* (2013.01); *H01L 41/29* (2013.01); *H01L 41/33* (2013.01); *A61B 8/12* (2013.01); *B06B 1/02* (2013.01); *B06B 1/0292* (2013.01); *B06B 1/06* (2013.01); *B06B 1/064* (2013.01); *B06B 1/0607* (2013.01); *G01S 15/8925* (2013.01); *G01S 15/8956* (2013.01); *Y10T 29/42* (2015.01); *Y10T 29/49005* (2015.01)

(58) Field of Classification Search
CPC ....... H01L 41/338; B06B 1/02; B06B 1/0292; B06B 1/06; B06B 1/0607; B06B 1/6022; B06B 1/0622; B06B 1/064; B61B 1/0604; Y10T 29/42; Y10T 29/49005
See application file for complete search history.

(56) References Cited

U.S. PATENT DOCUMENTS

| | | | |
|---|---|---|---|
| 5,065,068 A | 11/1991 | Oakley | |
| 5,311,095 A * | 5/1994 | Smith | B06B 1/064 |
| | | | 310/334 |
| 5,796,207 A | 8/1998 | Safari et al. | |
| 6,104,126 A | 8/2000 | Gilmore | |
| 6,255,761 B1 | 7/2001 | Benjarnin | |
| 6,278,224 B1 * | 8/2001 | Sawada | B06B 1/0622 |
| | | | 310/334 |
| 6,503,204 B1 | 1/2003 | Sumanaweera et al. | |
| 6,757,948 B2 | 7/2004 | Ptchelintsev et al. | |
| 6,806,622 B1 | 10/2004 | Schmidt et al. | |
| 6,984,284 B2 | 1/2006 | Yin et al. | |
| 7,377,900 B2 | 5/2008 | Vitek et al. | |
| 7,489,066 B2 | 2/2009 | Scott et al. | |
| 7,518,290 B2 | 4/2009 | Frey | |
| 7,758,509 B2 | 7/2010 | Angelsen et al. | |
| 8,310,133 B2 | 11/2012 | Brown et al. | |
| 8,823,246 B2 | 9/2014 | Brown et al. | |
| 2003/0216646 A1 | 11/2003 | Angelsen et al. | |
| 2005/0146247 A1 * | 7/2005 | Fisher | B06B 1/0292 |
| | | | 310/334 |
| 2006/0028099 A1 * | 2/2006 | Frey | H01L 41/08 |
| | | | 310/334 |
| 2007/0167815 A1 | 7/2007 | Jacobsen et al. | |
| 2008/0007142 A1 | 1/2008 | Toda | |
| 2008/0018199 A1 | 1/2008 | Trolier-McKinstry et al. | |
| 2009/0108708 A1 | 4/2009 | Jiang et al. | |
| 2009/0108710 A1 | 4/2009 | Brown et al. | |

OTHER PUBLICATIONS

International Searching Authority, International Search Report and Written Opinion, PCT Application PCT/IB2008/003874, dated Jul. 15, 2009, 8 pages.

Reynolds, P., et al. "Resonant Characteristics of Piezoelectric Composites: Analysis of Spurious Modes in Single and Multi-Element Ultrasonic Transducers," IEEE 2002 Ultrasonics Symposium, Oct. 8-11, 2002, pp. 1157-1160.

United States Patent and Trademark Office, Non-Final Office Action, U.S. Appl. No. 12/192,816, dated Jun. 8, 2010, 9 pages.

United States Patent and Trademark Office, Non-Final Office Action, U.S. Appl. No. 12/963,096, dated Sep. 27, 2011, 9 pages.

United States Patent and Trademark Office, Non-Final Office Action, U.S. Appl. No. 13/676,031, dated Jun. 17, 2013, 9 pages.

United States Patent and Trademark Office, Notice of Allowance, U.S. Appl. No. 12/963,096, dated Apr. 24, 2012, 8 pages.

United States Patent and Trademark Office, Notice of Allowance, U.S. Appl. No. 12/963,096, dated Jul. 11, 2012, 7 pages.

United States Patent and Trademark Office, Notice of Allowance, U.S. Appl. No. 13/676,031, dated Nov. 15, 2013, 9 pages.

* cited by examiner

METHODS OF MANUFACTURING HIGH FREQUENCY PIEZOCOMPOSITE ULTRASOUND TRANSDUCERS

This application is a continuation of U.S. patent application Ser. No. 13/676,031 filed on Nov. 13, 2012, now U.S. Pat. No. 8,823,246, which is a continuation of Ser. No. 12/963,096 filed on Dec. 8, 2010, now U.S. Pat. No. 8,310,133, which is a continuation of U.S. patent application Ser. No. 12/192,816 filed on Aug. 15, 2008, now abandoned, which claim the benefit of Provisional Application No. 60/983,263 filed on Oct. 29, 2007. The foregoing applications and patents are incorporated by reference herein in their entireties.

BACKGROUND OF THE INVENTION

Field of the Invention

This invention relates to piezoelectric composites, and more particularly to piezoelectric composites for high-frequency ultrasound applications and methods of manufacturing such composites.

Background Art

Typically, high quality medical imaging uses ultrasonic transducers or transducer arrays that posse the properties of good sensitivity and wide frequency bandwidth. Conventional transducers utilizing monolithic piezoelectric material such as, for example, lead zirconate titanate ("PZT"), typically exhibit a large acoustic impedance mismatch between the transducer and the medium under test, such as, for example, water, human tissue, and the like. To overcome this problem, piezoelectric composites that are made of individual small piezoelectric elements, which can be surrounded and isolated by a polymer matrix, such as, for example, epoxy, have been proposed and implemented at low frequencies. These small piezoelectric elements play an increasingly important role in the development of ultrasonic transducers for medical imaging. One commonly used structure of piezoelectric composite consists of small rectangular or square pillars of PZT that are embedded in a host matrix of polymer material. In one example, the height of the pillars normally about one half wavelength at the operating frequency if the backing material is lower in acoustic impedance.

Unfortunately, developing a high-frequency (>15 Hz) ultrasound transducer is also very challenging due to the extremely small pillar dimensions required in order to avoid significant lateral resonances in the piezoelectric composite. Conventionally, the design of piezo-composites is limited by the blade size limit of micro-dicing saws or other conventional apparatuses that are used to cut the bulk piezoelectric into composite pillars. It is very difficult using conventional dice and fill techniques to sufficiently reduce the size/spacing of the composite pillars enough to push the lateral resonances outside the operating bandwidth of a transponder that is configured to operate at high frequencies. For example, to push the first "lamb mode" frequency to about 80 MHz, while still maintaining a volume fraction of piezoelectric above 25%, a kerf width of approximately 6 µm is required (assuming a typical piezoelectric and epoxy filler). What is needed is a high-frequency ultrasound transducer that operatively suppresses these lateral modes within the piezoelectric composite.

In a further aspect, a lens is typically used to passively focus high-frequency ultrasound transducers. Developing a suitable acoustic lens, however, can be very challenging because the lens materials commonly used for lower frequency transducers are far too attenuating at frequencies at higher frequencies. Alternatively, the need for an acoustic lens can be avoided by geometrically curving the transducer. This can be accomplished by using a flexible piezo-composite material as the transducer substrate.

SUMMARY

In one aspect, the present application provides a transducer with triangular cross-sectional shaped pillars for suppressing lateral modes within a piezoelectric composite, and a method for producing the same.

A substrate having a longitudinal axis is provided. According to one aspect, a plurality of pillars is formed that extend outwardly from the substrate. In this aspect, the plurality of pillars can be positioned in adjacent rows that extend substantially parallel to the longitudinal axis of the substrate, forming an array of upright pillars. In one embodiment, each pillar can have a triangular cross-sectional shape formed from a pair of side walls and a base.

In one aspect, the array of pillars can comprise a plurality of paired pillars. In this aspect, each of the paired pillars comprises a first pillar positioned adjacent to a second pillar such that a base of the first pillar is spaced from and substantially opposes a base of the second pillar. Further, each row of the array of pillars can comprise a plurality of paired pillars that are positioned adjacent each other such that one side wall of the first pillar is spaced from and substantially opposes one side wall of the second pillar. In this embodiment, the triangular pillars and arrangement thereof are configured to operatively suppress the lateral modes of the transducer at higher operating frequencies, such as, at or above 15 MHz, at or above 20 MHz, or at or above 30 MHz.

In another aspect, a method of producing an ultrasonic wave emission pattern at higher operating frequencies, such as, at or above 15 MHz, at or above 20 MHz, or at or above 30 MHz, is provided. In this aspect, an electric signal can be applied to a piezoelectric substrate of a transducer, which has a plurality of triangular cross-sectional shaped pillars extending outwardly therefrom the substrate. The plurality of pillars can be positioned in rows substantially parallel to a longitudinal axis of the substrate to form an array of pillars. In one aspect, the array of pillars can comprised a plurality of paired pillars in which each of the paired pillars comprises a first pillar positioned adjacent to a second pillar such that a base of the first pillar is spaced from and substantially opposes a base of the second pillar. In a further aspect, it is contemplated that each row of the array of pillars can comprise a plurality of paired pillars that are positioned adjacent each other such that a side wall of the first pillar is spaced from and substantially opposes a side wall of the second pillar.

Additional advantages will be set forth in part in the description which follows, and in part will be obvious from the description, or may be learned by practice of the invention. It is to be understood that both the foregoing general description and the following detailed description are exemplary and explanatory only and are not restrictive of the invention.

BRIEF DESCRIPTION OF THE DRAWINGS

These and other features of the preferred embodiments of the invention will become more apparent in the following detailed description in which reference is made to the appended drawings wherein.

DETAILED DESCRIPTION OF THE INVENTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an," and "the" include plural referents unless the context clearly dictates otherwise. Thus, for example, reference to "a pillar" can include two or more such pillars unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Figure 1:
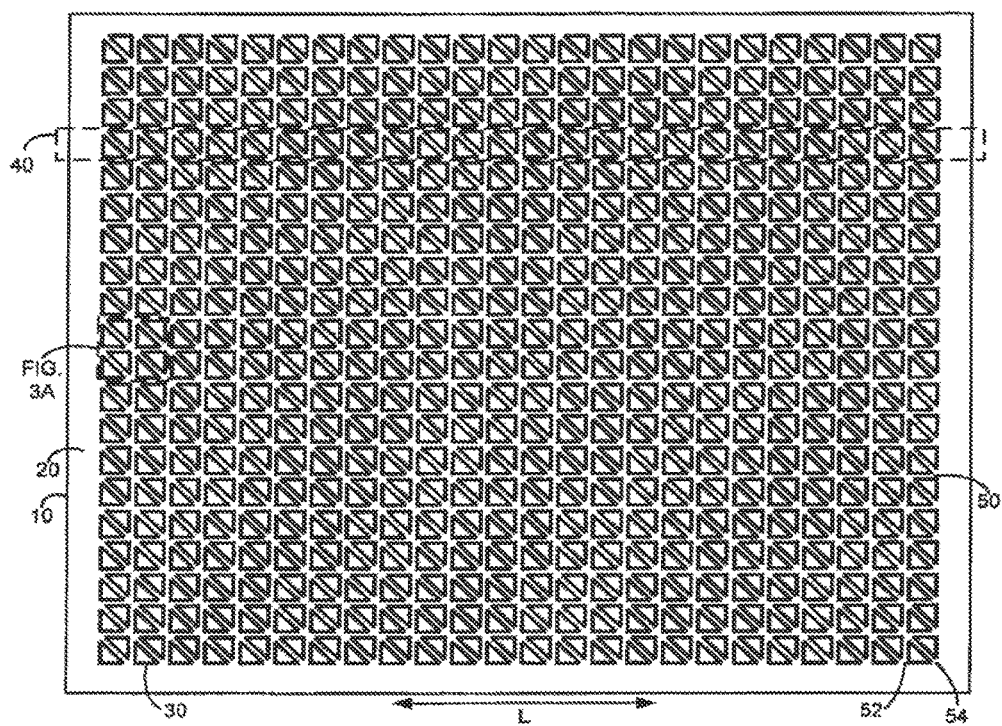
FIG. 1 is a schematic top elevational view of one embodiment of the transducer, showing the surface of a substrate and a plurality of pillars extending therefrom. In this aspect, the pillars have a substantially triangular cross-sectional shape. In one exemplary aspect, it is contemplated that the transducer can have a substantially planar cross-sectional shape. Optionally, it is contemplated that at least a portion of the transducer can have a curved or arcuate cross-sectional shape.
Figure 2A:
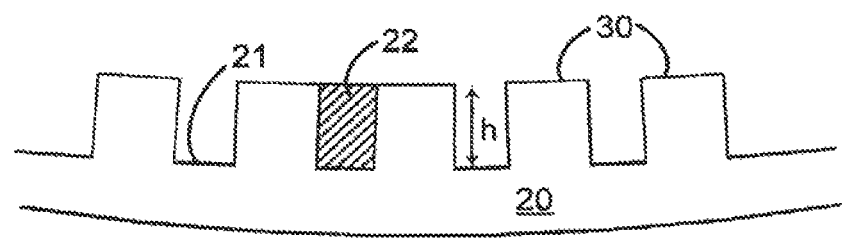
FIG. 2A is a partial cross-sectional view of the transducer of FIG. 1 taken across the longitudinal axis of FIG. 1, showing the substrate of the transducer having an arcuate cross-sectional shape.

As illustrated in FIGS. 1 and 2A, in one embodiment, a transducer 10 of the present application can comprise a substrate 20 and a plurality of pillars 30 extending outwardly from the substrate. The substrate has an upper surface 21 and a longitudinal axis. In one aspect, the substrate can be rigid. In another aspect, however, the substrate can be flexible. In yet another aspect, at least a portion of the substrate of the transducer can have a substantially planar cross-sectional shape. Optionally, it is contemplated that at least a portion of the transducer can have a curved or arcuate cross-sectional shape.

It is contemplated that the substrate can be formed from any desired material having the appropriate electrical and acoustical properties, as commonly known in the art. In one aspect, the substrate 20 can be formed from an electrostrictive material. In another aspect, the substrate can be formed from a piezoelectric material such as, for example and without limitation, lead zirconate titanate. In still another aspect and not meant to be limiting, the substrate can be formed from a single-crystal piezoelectric.

Figure 2B:
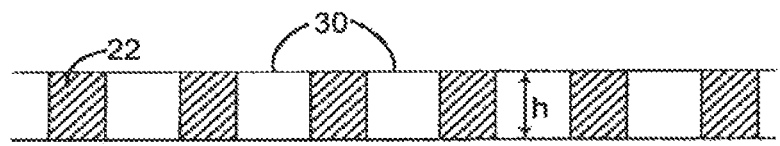
FIG. 2B is a partial cross-sectional view of the transducer of FIG. 2, showing the composite structure after the substrate is ground or lapped of the composite during fabrication and showing the formed pillars extending substantially from top to bottom to form a conventional 1-3 composite.

Referring to FIG. 2B, one skilled in the art will appreciate that it is contemplated that the solid thin layer of monolithic substrate 20 can be conventionally lapped or ground off in a final fabrication step. Thus, in this aspect, when this thin layer of solid substrate 20 is removed, the pillars extend substantially completely through the formed composite from top to bottom. In this example, the composite becomes a conventional 1-3 composite.

Optionally and referring to FIG. 2A, if the thin strip of substrate 20 is retained at the base of the pillars allows for ease in defining the array electrodes with precision, which allows for ease in operably connecting to the electrodes. Thus, in this aspect, if the thin strip of substrate 20 is retained, the composite formed in a 3-2 composite. One skilled in the art will appreciate that the exemplary 3-2 composite allows for precision definition of array electrodes due to the smooth and continuous bottom surface of the substrate 20, for example and without limitation, by using conventional photolithography techniques and also for ease of connectivity to the electrodes, for example and without limitation, by using conventional wire-bonding techniques. In another aspect, the exemplary substrate can be configured to be flexible such that the composite structure can be curved without fracturing the monolithic layer. Optionally, the monolithic layer can have a thickness that is configured to be thin enough in order to be able to curve the composite without fracturing the monolithic layer. In various examples, it is contemplated that the thickness of the monolithic layer (labelled as "20" in FIG. 2A) can be less than about 15 µm; alternatively less than about 10 µm; and optionally less than about 7 µm.

Figure 3A:
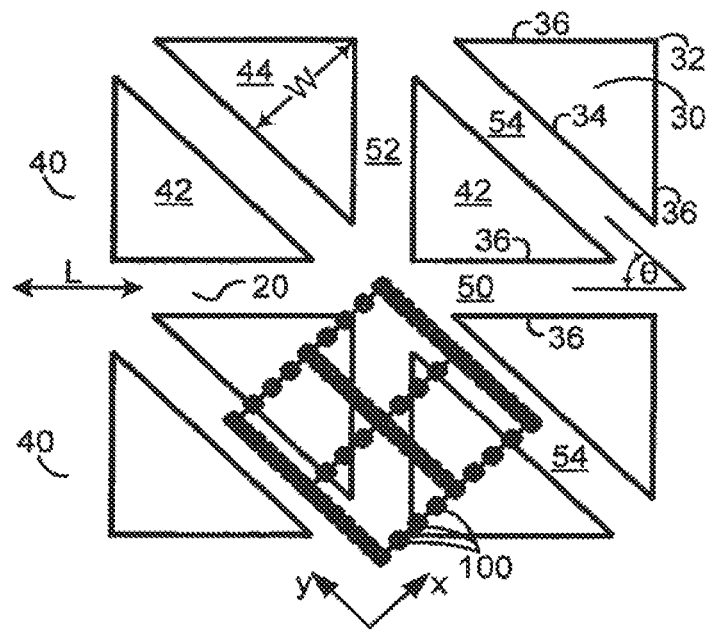
FIG. 3A is an enlarged top elevational view of a portion of the embodiment of the transducer shown in FIG. 1.

The pillars extend outwardly from the substrate 20. In one aspect, and as illustrated in FIGS. 1 and 3A, each pillar can have a triangular cross-sectional shape that has an apex 32, an opposed base 34 having opposed edges, and a pair of side walls 36 that extend from the apex to the respective edges of the base. In one exemplary aspect, each of the triangular pillars has an isosceles shape. Alternatively, each of the triangular pillars can have a right angle shape. Optionally, it is also contemplated that the pillars can have any generally triangular shape.

The plurality of pillars can be formed from any desired material having the appropriate electrical and acoustical properties, as commonly known in the art. In one aspect, the pillars 30 can be formed from an electrostrictive material. In another aspect, the pillars can be formed from a piezoelectric material such as, for example and without limitation, lead zirconate titanate. In still another aspect, the pillars can be formed from a single-crystal piezoelectric. In one exemplary aspect, the plurality of pillars can be formed from the same material as the substrate 20. Optionally the substrate and the pillars can be formed from a single-crystal piezoelectric.

In a further aspect, it is contemplated that each pillar extends substantially the same height (h) from the upper surface 21 of the substrate 20. Alternatively, it is contemplated that the pillars may vary in height. In various examples, it is contemplated that the height can range from between about 5 µm to 150 µm; alternatively from between about 20 µm to 70 µm; and optionally from between about 40 µm to 50 µm.

In a further aspect, it is contemplated that each pillar can have a width (w) from the base to the apex of the triangular shaped pillar that ranges from between about 40 um to 50 um; alternatively from between about 20 um to 60 um; and optionally from between about 5 um to 70 um.

According to one aspect, the plurality of pillars 30 can form an array of pillars positioned in adjacent rows 40, as illustrated in FIG. 1. In one aspect, each row of the array of pillars can extend substantially parallel to the longitudinal axis of the substrate 20. Referring to FIG. 3A, in another aspect the array of pillars can comprise a plurality of paired pillars. In this exemplary aspect, each of the paired pillars can comprise a first pillar 42 positioned adjacent to a second pillar 44 such that the base 34 of the first pillar is spaced from and substantially opposes the base of the second pillar. Further, in this exemplary aspect, each row 40 of the array of pillars can comprise a plurality of paired pillars that are positioned adjacent each other such that one side wall 36 of the first pillar 42 is spaced from and substantially opposes one side wall of the second pillar 44.

As exemplarily illustrated in FIGS. 1 and 3A, in one aspect, the array of pillars can define a plurality of first troughs or kerfs 50 that extend substantially parallel to the longitudinal axis of the substrate 20 and a plurality of second troughs or kerfs 52 that extend substantially transverse to the longitudinal axis of the substrate. Further, the array of pillars can define a plurality of third troughs or kerfs 54 that extend at an acute angle θ relative to the longitudinal axis of the substrate. In a further aspect, it is contemplated that acute angle θ can range from between about 20° to 70°; alternatively from between about 30° to 60°; and optionally from between about 40° to 50°. In another aspect, the width of the first trough can be substantially the same as the width of the second trough, and the width of the second trough 52 can be substantially the same as the width of the third trough. Of course, it is also contemplated that the widths of the respective troughs or kerfs can vary in width dimension.

In a further aspect, it is contemplated that each trough or kerf has a width that ranges from between about 1 um to 20 um; alternatively from between about 5 um to 17 um; and optionally from between about 10 µm to 15 µm. In yet another aspect, it is contemplated that the transponder can be configured such the PZTH5H or single crystal volume fraction ranges from between about 10% to 75%; alternatively from between about 15% to 50%; and optionally from between about 20% to 30.

In yet another aspect, at least a portion of the respective first, second, and third troughs can be at least partially filled with a fill material 22. The fill material can comprise, for example and without limitation, a polymeric material, such as loaded epoxy, polymer micro-spheres, crystal bond, photoresist material and the like, as is customary and standard practice in the manufacture of composite transducers. In one exemplary aspect, the fill material may be SU8 photoresist. Optionally, fill material can comprise a PZT powder. Alternatively, in one aspect, the respective first, second, and third troughs can be left, at least in part, unfilled. One will appreciate that the troughs may not be completely filled or that they may only be filled temporarily as some or the entire trough filling material can removed using conventional methods.

With reference to FIGS. 1-3A and 3C, a transducer can be fabricated to comprise any or all of the features as described above. In one aspect, the substrate 20 can be diced with a dicing saw. A first cutting operation can be performed into the substrate substantially parallel to the longitudinal axis of the substrate so that the plurality of first troughs 50 is defined in the planar upper surface 21 of the substrate. A second cutting operation can be performed into the substrate substantially transverse to the longitudinal axis of the substrate so that the plurality of second troughs 52 is also defined in the planar upper surface of the substrate 20. A third cutting operation can be performed onto the upper surface of the substrate at the acute angle θ relative to the longitudinal axis of the substrate so that the plurality of third troughs 50 are defined in the planar upper surface 21 of the substrate. The cutting operations can be performed so that a plurality of pillars 30 extend outwardly from the substrate 20 as described above, forming an array of pillars.

According to various aspects, the first, second, and third troughs can then be at least partially filled with a fill material, for example and without limitation, comprising SU8 photoresist PZT powder, and the like. Next, the fill material can be cured, as is known in the arts. The substrate 20, plurality of pillars and/or fill material can be ground, lapped, or otherwise removed until the desired thickness is achieved. In one exemplary aspect, the thickness of the substrate 20, plurality of pillars and/or fill material can be between 10 and 100 µm. In one exemplary aspect, the thickness of the substrate, plurality of pillars 30 and/or fill material can be about 40-50 µm. In another aspect, the composite structure can have a fill material volume fraction of between 10% and 50%. In one exemplary aspect and in consideration of the maintenance of a desirable electromechanical coupling coefficient, the fill material volume fraction can be about 20% to 30%.

According to other aspects, at least a portion of the substrate 20, plurality of pillars and/or fill material can be formed into a spherical geometry having a radius of curvature between 1 and 50 mm. In another aspect, the substrate, plurality of pillars 30 and/or fill material can be formed into a spherical geometry having a radius of curvature of about 9 mm. The substrate, plurality of pillars and/or fill material can then be mounted into an SMA connector using a conductive backing epoxy, as commonly known in the arts. Finally, the transducer 10 can be machined down to a desired diameter and a ground electrode can be evaporated onto a front face of the transducer. The desired diameter of the transducer, in one exemplary aspect, can be between 1 and 10 mm. In a further exemplary aspect, the desired diameter of the transducer can be about 3 mm.

Figure 3B:
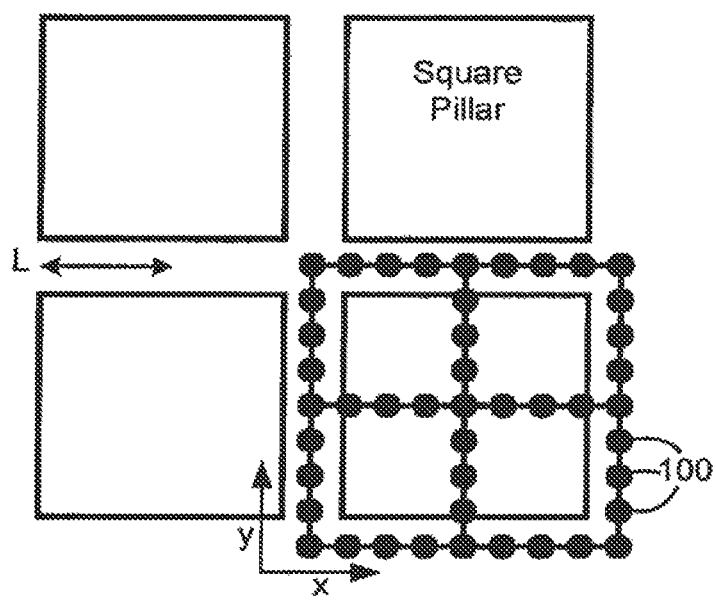
FIG. 3B is an enlarged top elevational view of a conventional, prior art transducer with square cross-sectional shaped pillars.
Figure 3C:
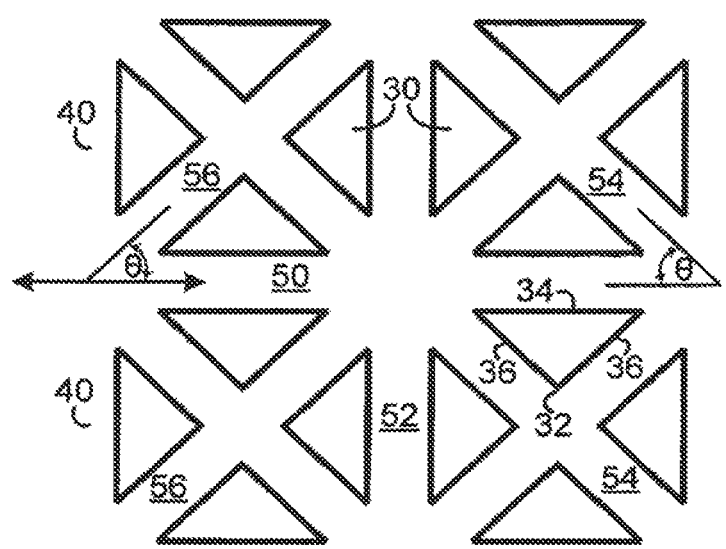
FIG. 3C is an enlarged top elevational view of an alternative embodiment of the transducer with triangular cross-sectional shaped pillars.

In other embodiments and as shown in FIG. 3C, the transducer 10 of the current application can comprise a plurality of pillars 30 for emitting energy in response to an input signal. The plurality of pillars can be positioned in adjacent, substantially parallel rows, wherein each pillar has a substantially triangular cross-sectional shape for suppressing the lateral modes at the operating frequencies. Each pillar can have an apex 32, an opposed base 34 having opposed edges, and a pair of side walls 36 that extend from the apex to the respective edges of the base. In this aspect, the plurality of pillars can comprise of a plurality of paired pillars, wherein each of the paired pillars comprises a first pillar 42 positioned adjacent to a second pillar 44 such that the base of the first pillar is spaced from and substantially opposes the base of the second pillar. Further, each row of the array of pillars can comprise a plurality of paired pillars that are positioned adjacent each other such that one side wall of the first pillar is spaced from and substantially opposes one side wall of the second pillar.

In this exemplary embodiment, the transducer can further comprise a substrate 20 that is at least partially curved. It is contemplated that the substrate and the plurality of pillars can form an electrically monolithic structure, which is configured for emitting energy in response to the input signal. The array of pillars can define a plurality of first troughs 50 extending substantially parallel to a longitudinal axis of the substrate, a plurality of second troughs 52 extending substantially transverse to the longitudinal axis of the substrate, and a plurality of third troughs 54 extending at an acute angle θ relative to the longitudinal axis of the substrate. In one aspect, the width of the respective first, second, and third troughs can be substantially equal. In another aspect, at least a portion of the respective first, second, and third troughs can be at least partially filled with a fill material.

In another embodiment, the transducer 10 of the current application can comprise a substrate 20 having a longitudinal axis, a plurality of pillars 30 extending outwardly therefrom the substrate, and a means for suppressing the lateral modes of the transducer at higher operating frequencies, such as, at or above 15 MHz, at or above 20 MHz, or at or above 30 MHz. In one aspect, at least a portion of the substrate 20 can be flexible. In another aspect, at least a portion of the substrate can be curved in cross-section such that the transducer is geometrically curved. In yet another aspect, the substrate and the plurality of pillars 30 can be formed from a single-crystal piezoelectric or from a piezoelectric material such as, for example lead zirconate titanate.

In yet another aspect, the plurality of pillars can form an array of pillars positioned in adjacent rows 40, wherein each row of the array of pillars extends substantially parallel to the longitudinal axis of the substrate. In yet another aspect, the means for suppressing the lateral modes can comprise each pillar 30 having a triangular cross-sectional shape that has an apex 32, an opposed base 34 having opposed edges, and a pair of side walls 36 that extend from the apex to the respective edges of the base. In one example, the array of pillars can define a plurality of first troughs 50 extending substantially parallel to the longitudinal axis of the substrate, a plurality of second troughs 52 extending substantially transverse to the longitudinal axis of the substrate, a plurality of third troughs 54 extending at about an acute angle θ relative to the longitudinal axis of the substrate, such as, for example and not meant to be limiting, a 45° angle. Optionally, a plurality of fourth troughs 56 can be formed that each extends substantially transverse to the third troughs.

In this embodiment, in one aspect, the width of the first trough can be substantially the same as the width of the second trough. In another aspect, the width of the second trough 52 can be substantially the same as the width of the third trough. In a further aspect, the width of the third trough can be substantially the same as the width of the fourth trough. In yet another aspect, at least a portion of the respective first, second, third, and fourth troughs can be at least partially filled with a fill material 22. The fill material can comprise, for example, a polymeric material, such as, for example, loaded epoxy, polymer micro-spheres, crystal bond, photoresist material and the like, as is customary and standard practice in the manufacture of composite transducers, or they may be left, at least in part, unfilled. In one exemplary aspect, the fill material can be, for example and without limitation, SU8 photoresist, PZT powder, and the like.

In yet another embodiment, a method of producing an ultrasonic wave emission pattern at higher operating frequencies, such as, at or above 15 MHz, at or above 20 MHz, or at or above 30 MHz, is provided. In one aspect, the method can comprise applying an electric signal to a piezoelectric substrate of a transducer 10 having a plurality of pillars 30 extending outwardly therefrom the substrate 20. The lateral modes of the transducer can be suppressed by providing each pillar 30 with a triangular cross-sectional shape that has an apex 32, an opposed base 34 having opposed edges, and a pair of side walls 36 that extend from the apex to the respective edges of the base. In one aspect, the array of pillars can comprise a plurality of paired pillars, wherein each of the paired pillars comprises a first pillar 42 positioned adjacent to a second pillar 44 such that the base of the first pillar is spaced from and substantially opposes the base 34 of the second pillar. In another aspect, each row 40 of the array of pillars can comprise a plurality of paired pillars that are positioned adjacent each other such that one side wall of the first pillar is spaced from and substantially opposes one side wall 36 of the second pillar.

In this embodiment, the array of pillars can define a plurality of first troughs 50 extending substantially parallel to a longitudinal axis of the substrate, a plurality of second troughs 52 extending substantially transverse to the longitudinal axis of the substrate, and a plurality of third troughs 54 extending at an acute angle θ relative to the longitudinal axis of the substrate. In one aspect, the width of the respective first, second and third troughs can be substantially equal. In another aspect, at least a portion of the respective first, second, and third troughs can be at least partially filled with a fill material. In yet another aspect, the substrate can be flexible.

In use, in one aspect, the transducer 10 is configured, at higher operating frequencies, such as, at or above 15 MHz, at or above 20 MHz, or at or above 30 MHz, can spread the lateral energy out over a broad spectrum of frequencies. At these higher operating frequencies, the triangular cross-sectional shape of the plurality of pillars 30 can remove or suppress virtually all of the lateral modes within the individual pillars and can break up the pillar-to-pillar periodicities that can cause spurious modes. Further, the spread in lateral energy can also help to rapidly dampen secondary ringing in the thickness mode.

EXAMPLE

In order to demonstrate the efficacy of the transducer described herein, two sample transducers were prepared and tested, as described below. Example 1 was a transducer having a plurality of pillars having a triangular cross-sectional shape, as described herein. The triangular pillars were isosceles in shape and arranged in the pattern shown in FIG. 3A. Example 2 was a transducer having a plurality of pillars having a square cross-sectional shape, as is known in the art, and as shown in FIG. 3B. Each composite structure had 15 μm troughs, a 42 μm pillar height, and a fill material volume fraction of approximately 25%. FIGS. 3A and 3B show the arrangement of both composite structures as well as identifying different points on the exemplary transducers that were closely analyzed.

Figure 4A:
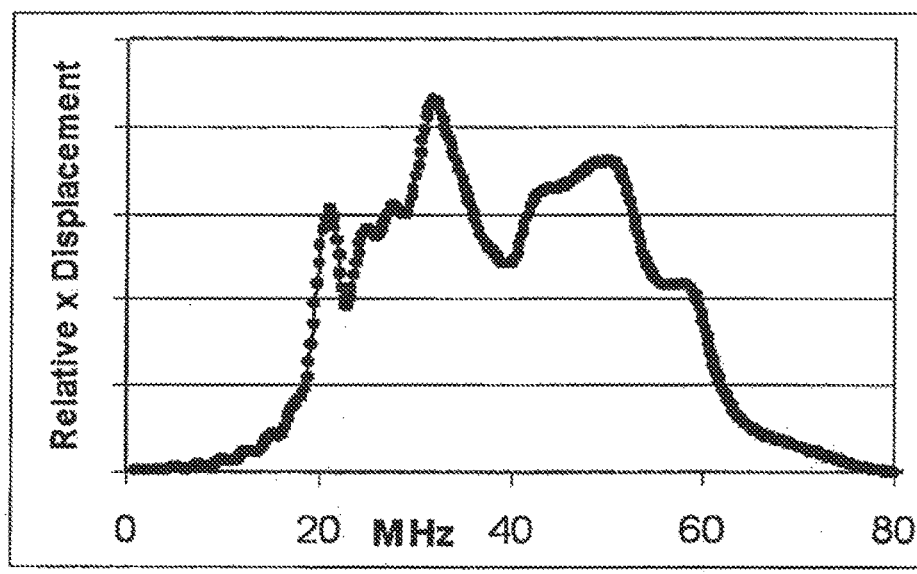
FIG. 4A is a chart showing the sum of the lateral displacement spectra of all points labelled on the transducer of FIG. 3A with triangular cross-sectional shaped pillars.
Figure 4B:
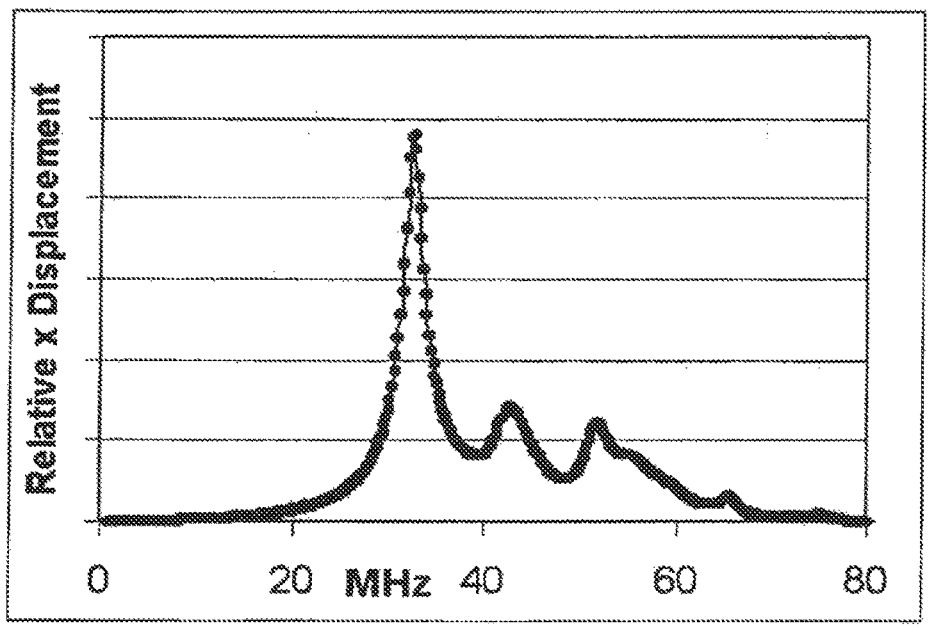
FIG. 4B is a chart showing the sum of the lateral displacement spectra of all points labelled on the conventional transducer of FIG. 3B with square cross-sectional shaped pillars.

For each point marked on the respective FIGS. 3A and 3B, the displacements were simulated in all three dimensions when excited with a monocycle excitation pulse in the thickness dimension. To analyze the lateral modes, the displacements 100 for each point were summed in the frequency domain. FIGS. 4A and 4B show the displacements 100 summed together for the x direction. As can be seen in FIGS. 4A and 4B, the square-pillar composite design (FIG. 4B) possesses lateral displacements in much narrower bands than the triangular-pillar composite (FIG. 4A).

Figure 5A:
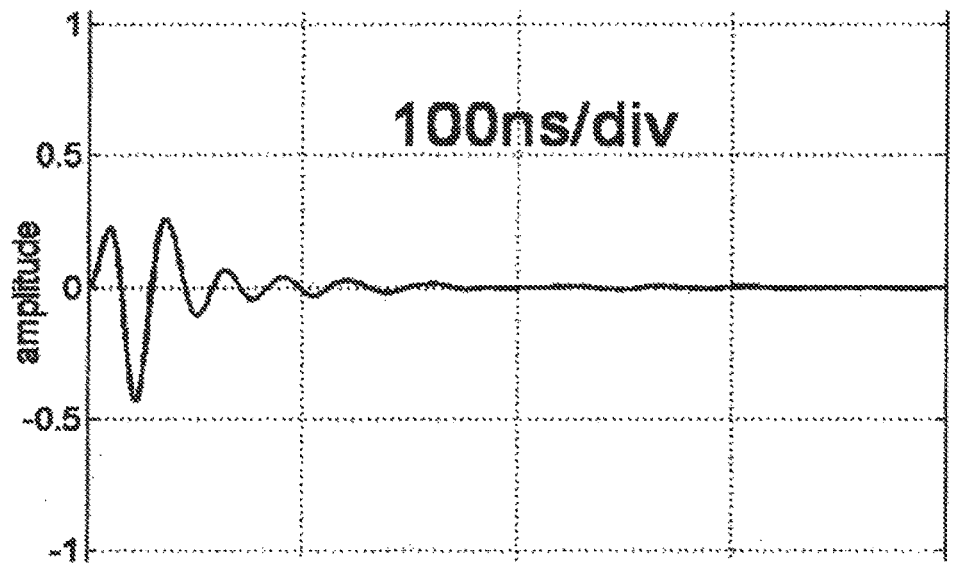
FIG. 5A is a chart showing the simulated one-way pulse responses using PZFlex for an exemplary triangular cross-sectional shaped pillar.
Figure 5B:
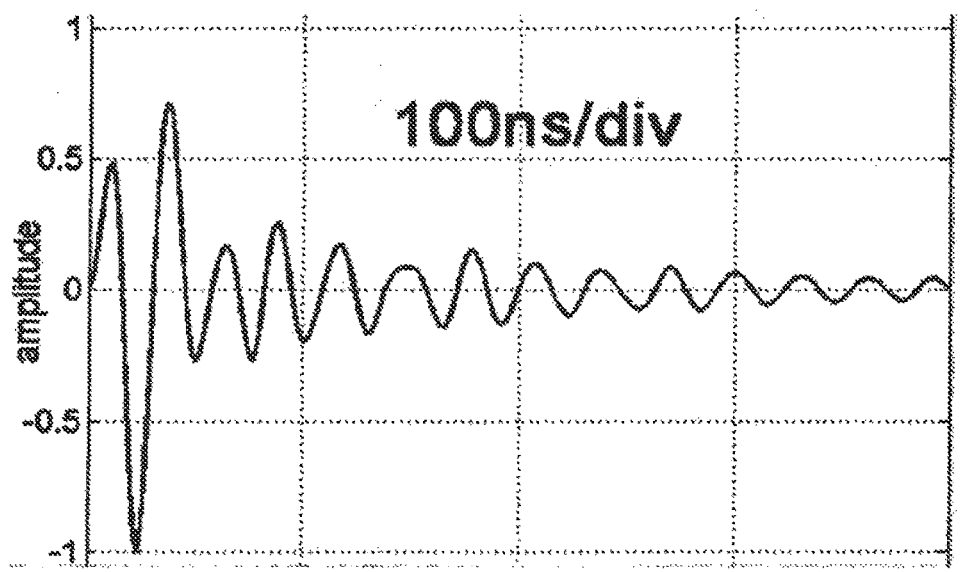
FIG. 5B is a chart showing the simulated one-way pulse responses using PZFlex for an exemplary conventional square cross-sectional shaped pillar.
Figure 6A:
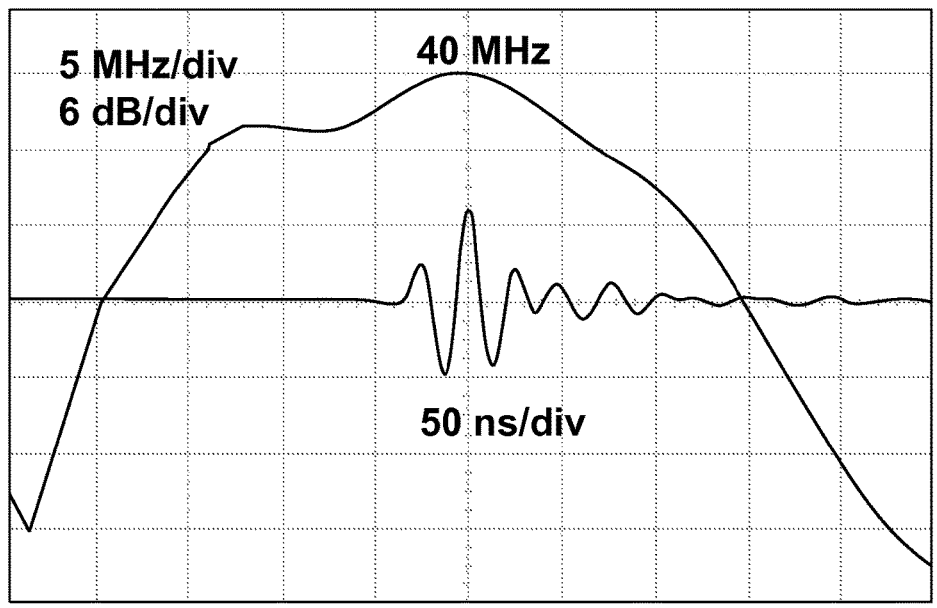
FIG. 6A is a chart showing the simulated two-way pulse-echo responses using PZFlex for an exemplary triangular cross-sectional shaped pillar.
Figure 6B:
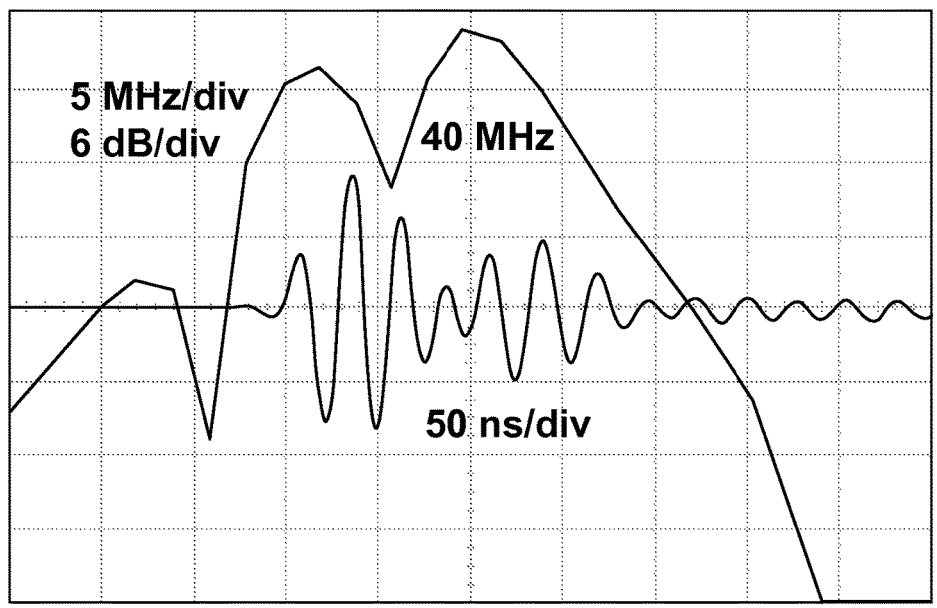
FIG. 6B is a chart showing the simulated two-way pulse-echo responses using PZFlex for an exemplary conventional square cross-sectional shaped pillar.
Figure 7:
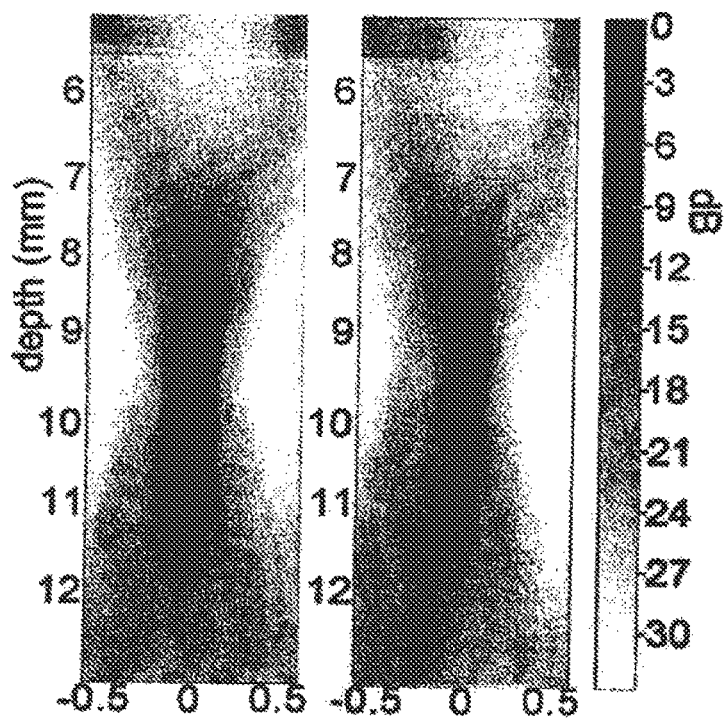
FIG. 7 is an image of a one-way measured radiation pattern for an exemplary triangular cross-sectional shaped pillar.
Figure 8:
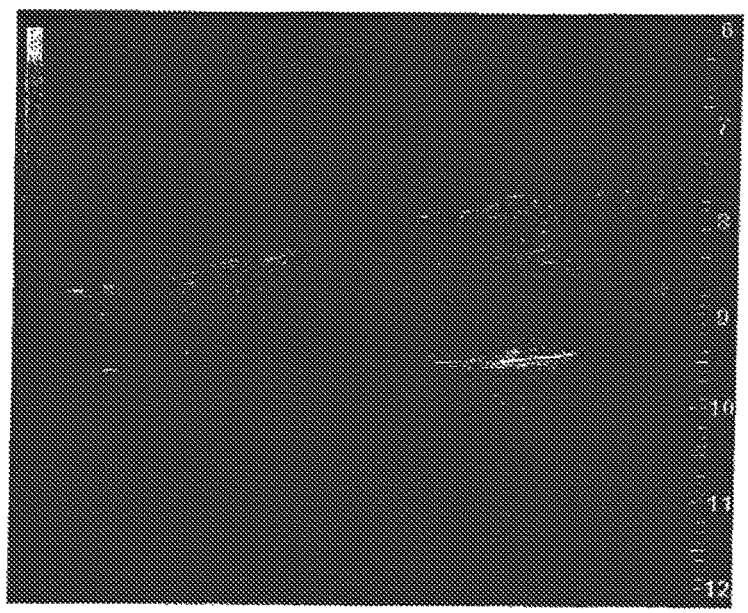
FIG. 8 is an image of a human finger generated with an exemplary transducer having a plurality of triangular cross-sectional shaped pillars thereon.

To evaluate the performance of both transducers, the following characteristics were measured: electrical impedance, pulse-echo response, and one-way radiation pattern. The electrical impedance magnitude at 40 MHz was measured to be 9 ohms for the square-pillar composite and 11 ohms for the triangular cross-sectional shaped pillar composite. The −6 dB pulse echo bandwidths were measured to be 20% for the square-pillar composite and 55% for triangular cross-sectional shaped pillar composite. The pulses are shown in the form of oscilloscope screen captures in FIGS. 5A and 5B. The pulse echoes were generated by situating a quartz flat in font of the transducers at the geometric focus. The pulse amplitude for the square-pillar composite was measured to be 5.5 dB more sensitive than the triangular cross-sectional shaped pillar composite. The peak insertion losses of the two composites were measured to be approximately −25 dB for the square-pillar and −31 dB for the triangular cross-sectional shaped pillar composite. The one-way radiation pattern for the triangular cross-sectional shaped pillar composite was then measured by scanning a needle hydrophone in front of the transducer in all three dimensions. FIG. 7 shows the resulting radiation pattern in two perpendicular planes (x, y planes). The average −3 dB beamwidth was measured to be 120 μm and the −3 dB depth-of-field was measured to be 2.5 mm.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of fabricating an ultrasound transducer, the method comprising:
    forming a first trough in a transducer substrate in a first direction substantially parallel to a longitudinal axis of the substrate, wherein the transducer substrate is configured to emit ultrasound energy at a frequency of 15 Megahertz (MHz) or greater;
    forming a second trough in the transducer substrate in a second direction substantially perpendicular to the longitudinal axis of the substrate;
    forming a third trough in the transducer substrate in a third direction at an acute angle to the longitudinal axis of the substrate; and
    forming a fourth trough in the transducer substrate in a fourth direction that is transverse to the third direction.

2. The method of claim 1 wherein the steps of forming the first, second, third and fourth troughs defines a group of pillars on the transducer substrate arranged to suppress lateral modes at transducer operating frequencies of at least 15 MHz.

3. The method of claim 1 wherein forming the first trough comprises forming the first trough with a width, and wherein forming the second trough comprises forming the second trough with a width substantially the same as the width of the first trough.

4. The method of claim 1, further comprising filling at least a portion of at least one of the first trough, the second trough, the third trough and the fourth trough with a fill material.

5. The method of claim 4 wherein the fill material comprises a loaded epoxy.

6. The method of claim 4 wherein the fill material is a photoresist material.

7. The method of claim 1, further comprising geometrically curving at least a lower surface of the transducer substrate.

8. The method of claim 7 wherein geometrically curving at least a portion of the transducer substrate comprises forming the transducer substrate in a spherical geometry having a radius of curvature between about 1 mm and about 50 mm.

9. A method of fabricating an ultrasound transducer, the method comprising:
    forming a plurality of first troughs in a transducer substrate in a first direction substantially parallel to a longitudinal axis of the substrate, wherein the transducer substrate is configured to emit ultrasound energy at a frequency greater than 15 Megahertz (MHz);
    forming a plurality of second troughs in the transducer substrate in a second direction substantially perpendicular to the longitudinal axis of the substrate;
    forming a plurality of third troughs in the transducer substrate in a third direction oblique to the longitudinal axis of the transducer substrate; and forming a plurality of fourth troughs in the transducer substrate in a fourth direction that is transverse to the third direction.

10. The method of claim 9 wherein the first troughs, the second troughs, the third troughs and the fourth troughs each have widths between about 5 microns and about 20 microns.

11. The method of claim 10, further comprising filling at least a portion of one or more of the first troughs, the second troughs, the third troughs and the fourth troughs with a fill material.

12. The method of claim 9 wherein the steps of forming the first, second and third troughs defines a group of pillars on the transducer substrate arranged to suppress lateral modes at transducer operating frequencies of at least 15 MHz.

13. A method of fabricating an ultrasound transducer, the method comprising:
    forming a plurality of first troughs in a transducer substrate in a first direction, wherein the transducer substrate has a center operating frequency of 15 MHz or higher;
    forming a plurality of second troughs in the transducer substrate in a second direction orthogonal to the first direction;
    forming a plurality of third troughs in the transducer substrate in a third direction oriented at an acute angle relative to the first direction; and
    forming a plurality of fourth troughs in a fourth direction transverse to the third direction.

14. The method of claim 13, further comprising:
    at least partially filling the first, second, third and fourth troughs with an uncured fill material;
    allowing the uncured fill material to cure, thereby forming a cured filling material; and
    removing a portion of the cured fill material from the first, second and third troughs.

15. The method of claim 13, further comprising geometrically curving at least a lower surface of the transducer substrate.

16. The method of claim 13 wherein forming the plurality of third troughs comprises performing a cutting operation at an angle between 20 degrees and 70 degrees relative to a longitudinal axis of the transducer substrate.

17. An ultrasound transducer, comprising:
    a first trough in a transducer substrate in a first direction substantially parallel to a longitudinal axis of the substrate, wherein the transducer substrate is configured to emit ultrasound energy at a frequency of 15 Megahertz (MHz) or greater;
    a second trough in the transducer substrate in a second direction substantially perpendicular to the longitudinal axis of the transducer substrate;
    a third trough in the transducer substrate in a third direction at an acute angle with respect to the longitudinal axis of the substrate; and
    a fourth trough in the transducer substrate in a fourth direction that is transverse to the third direction.

18. An ultrasound transducer, comprising:
    a transducer substrate configured to emit ultrasound energy at a center frequency of 15 MHz or higher;
    a plurality of first troughs in the transducer substrate in a first direction;
    a plurality of second troughs in the transducer substrate in a second direction orthogonal to the first direction;
    a plurality of third troughs in the transducer substrate in a third direction oriented at an acute angle relative to the first direction; and
    a plurality of fourth troughs in a fourth direction transverse to the third direction.

* * * * *

UNITED STATES PATENT AND TRADEMARK OFFICE
CERTIFICATE OF CORRECTION

PATENT NO. : 9,997,696 B2
APPLICATION NO. : 14/203435
DATED : June 12, 2018
INVENTOR(S) : Jeremy Brown et al.

It is certified that error appears in the above-identified patent and that said Letters Patent is hereby corrected as shown below:

On the Title Page

On the page 2, in item (63), in Column 1, in "Related U.S. Patent Documents", Line 3, delete "continuation-in-part" and insert -- continuation --, therefor.

In the Specification

In Column 9, Line 56, delete "font" and insert -- front --, therefor.

Signed and Sealed this
Twentieth Day of November, 2018

Andrei Iancu
*Director of the United States Patent and Trademark Office*